(12) United States Patent
Mori

(10) Patent No.: US 10,422,756 B2
(45) Date of Patent: Sep. 24, 2019

(54) SEMICONDUCTOR WAFER EVALUATION METHOD AND SEMICONDUCTOR WAFER

(71) Applicant: SUMCO CORPORATION, Tokyo (JP)

(72) Inventor: Keiichiro Mori, Saga (JP)

(73) Assignee: SUMCO CORPORATION, Tokyo (JP)

( * ) Notice: Subject to any disclaimer, the term of this patent is extended or adjusted under 35 U.S.C. 154(b) by 0 days.

(21) Appl. No.: 15/765,857

(22) PCT Filed: Aug. 23, 2016

(86) PCT No.: PCT/JP2016/074471
§ 371 (c)(1),
(2) Date: Apr. 4, 2018

(87) PCT Pub. No.: WO2017/061179
PCT Pub. Date: Apr. 13, 2017

(65) Prior Publication Data
US 2018/0292330 A1 Oct. 11, 2018

(30) Foreign Application Priority Data
Oct. 7, 2015 (JP) .................................. 2015-199111

(51) Int. Cl.
*G01N 21/94* (2006.01)
*G01N 21/88* (2006.01)
(Continued)

(52) U.S. Cl.
CPC ............ *G01N 21/94* (2013.01); *G01N 21/88* (2013.01); *G01N 21/9501* (2013.01); *G01N 21/956* (2013.01); *G02B 5/3075* (2013.01)

(58) Field of Classification Search
CPC ... G01N 21/94; G01N 21/9501; G02B 5/3075
(Continued)

(56) References Cited

U.S. PATENT DOCUMENTS 6,894,302 B2 * 5/2005 Ishimaru ............. G01N 21/474
250/559.41
8,169,613 B1 5/2012 Biellak et al.
(Continued)

FOREIGN PATENT DOCUMENTS

JP    H11-64234 A     3/1999
JP    2000-162141 A   6/2000
(Continued)

OTHER PUBLICATIONS

International Search Report issued in WIPO Patent Application No. PCT/JP2016/074471, dated Nov. 8, 2016.
(Continued)

*Primary Examiner* — Tri T Ton
(74) *Attorney, Agent, or Firm* — Greenblum & Bernstein, P.L.C.

(57) ABSTRACT

A method of evaluating a semiconductor wafer, which has a polished surface, by using a laser surface-inspection device including incident and light-receiving systems, includes evaluating the semiconductor wafer by detecting, as a light point defect, an abnormality of a process-induced defect and a surface-adhered foreign matter present on the polished surface of the semiconductor wafer, on the basis of measurement result obtained by directing incident light to the polished surface of the semiconductor wafer from one incident system and receiving, with a first light-receiving system, radiation light which has been radiated by the incident light being reflected or scattered by the polished surface, measurement result obtained by receiving the radiation light with a second light-receiving system, and measurement result obtained by receiving the radiation light with a third light-receiving system, and at least one of a light-receiving angle and polarization selectivity differs among the first, second and third light-receiving systems.

6 Claims, 4 Drawing Sheets

(51) Int. Cl.
*G01N 21/956* (2006.01)
*G01N 21/95* (2006.01)
*G02B 5/30* (2006.01)

(58) Field of Classification Search
USPC ............... 356/237.1–237.6, 239.1–239.8
See application file for complete search history.

(56) References Cited

U.S. PATENT DOCUMENTS

| | | | |
|---|---|---|---|
| 9,633,913 | B2 | 4/2017 | Mori |
| 2001/0030296 | A1 | 10/2001 | Ishimaru et al. |
| 2001/0048523 | A1 | 12/2001 | Fossey et al. |
| 2002/0041374 | A1* | 4/2002 | Ohshima ............ G01N 21/8806 356/237.2 |
| 2003/0071992 | A1 | 4/2003 | Fossey et al. |
| 2004/0085533 | A1 | 5/2004 | Fossey et al. |
| 2005/0185172 | A1 | 8/2005 | Ishimaru et al. |
| 2007/0121108 | A1 | 5/2007 | Ishimaru et al. |
| 2009/0103078 | A1 | 4/2009 | Ishimaru et al. |
| 2010/0004875 | A1 | 1/2010 | Urano et al. |
| 2012/0069329 | A1 | 3/2012 | Ishimaru et al. |
| 2012/0092484 | A1* | 4/2012 | Taniguchi ......... G01N 21/9501 348/87 |
| 2013/0258327 | A1 | 10/2013 | Kusaka et al. |
| 2014/0218723 | A1 | 8/2014 | Ishimaru et al. |

FOREIGN PATENT DOCUMENTS

| | | |
|---|---|---|
| JP | 2001-503148 A | 3/2001 |
| JP | 2001-255278 A | 9/2001 |
| JP | 2001-313321 A | 11/2001 |
| JP | 2002-257747 A | 9/2002 |
| JP | 2010-014635 A | 1/2010 |
| JP | 2010-129748 A | 6/2010 |
| JP | 2013-205239 A | 10/2013 |
| JP | 5509581 B2 | 6/2014 |
| JP | 2015-516574 A | 6/2015 |
| WO | 98/25131 A1 | 6/1998 |
| WO | 2013/155008 A1 | 10/2013 |

OTHER PUBLICATIONS

International Preliminary Report on Patentability issued in WIPO Patent Application No. PCT/JP2016/074471, dated Apr. 10, 2018.
Office Action issued in Japan Counterpart Patent Appl. No. 2015-199111, dated Aug. 28, 2018 , along with an english translation thereof.
Office Communication issued in Korea Patent Appl. No. 10-2018-7008415, dated May 28, 2019, along with an English translation thereof.

* cited by examiner

SEMICONDUCTOR WAFER EVALUATION METHOD AND SEMICONDUCTOR WAFER

CROSS-REFERENCE TO RELATED APPLICATIONS

This application claims the benefit of priority to Japanese Patent Application No. 2015-199111 filed on Oct. 7, 2015, which is expressly incorporated herein by reference in its entirety.

TECHNICAL FIELD

The present invention relates to a semiconductor wafer evaluation method, and more specifically relates to a method of evaluating a semiconductor wafer having a polished surface.

The present invention further relates to a semiconductor wafer which has a polished surface and has been evaluated by the above evaluation method.

BACKGROUND ART

As the evaluation method for a defect of a semiconductor wafer or for a foreign matter adhering to the surface of a semiconductor wafer, a method based on a light point defect (LPD) detected by a laser surface-inspection device is widely used (for example, see Japanese Patent No. 5509581, which is expressly incorporated herein by reference in its entirety). In this method, light is directed to the surface of a semiconductor wafer to be evaluated, and the radiation light (scattering light and reflection light) from this surface is detected to evaluate the presence or absence and/or size of a defect/foreign matter of the semiconductor wafer.

SUMMARY OF THE INVENTION

Among semiconductor wafers, a polished wafer is a semiconductor wafer which is produced through various types of steps including a polishing step, and the surface (uppermost surface) thereof is a polished surface. Here, the polished surface means a surface on which mirror polishing (referred to also as mirror finish) has been performed. On the surface (polished surface) of a polished wafer, there may be a surface-adhered foreign matter and a defect (hereinafter, referred to as a "process-induced defect") generated due to mirror polishing and/or various types of steps performed before/after the mirror polishing. If these surface-adhered foreign matter and process-induced defect can be detected, a polished wafer having few process-induced defects/surface-adhered foreign matters can be provided by controlling the manufacturing process, such as by removing the causes of the surface-adhered foreign matter and process-induced defect on the basis of the detection result.

An aspect of the present invention provides for a new evaluation method for evaluating a semiconductor wafer having a polished surface by detecting process-induced defects/surface-adhered foreign matters.

A laser surface-inspection device includes an incident system and a light-receiving system. In this connection, Japanese Patent No. 5509581 describes an approach of detecting defects and foreign matters introduced in the polishing step by using a laser surface-inspection device provided with two types of incident systems. In contrast, the present inventor has newly discovered, as the results of repeating intensive studies, the following evaluation method using incident light from one incident system:

a method of evaluating a semiconductor wafer having a polished surface by using a laser surface-inspection device including incident and light-receiving systems, which includes evaluating the semiconductor wafer by detecting, as a light point defect, an abnormality selected from the group consisting of a process-induced defect and a surface-adhered foreign matter present on the polished surface of the semiconductor wafer, on the basis of measurement result 1 obtained by directing incident light to the polished surface of the semiconductor wafer from one incident system and receiving, with a first light-receiving system, radiation light which has been radiated by the incident light being reflected or scattered by the polished surface, measurement result 2 obtained by receiving the radiation light with a second light-receiving system, and measurement result 3 obtained by receiving the radiation light with a third light-receiving system, wherein at least one selected from the group consisting of a light-receiving angle and polarization selectivity differs among the first light-receiving system, the second light-receiving system, and the third light-receiving system.

That is, with the above evaluation method, it is possible to detect the above abnormalities on the basis of three types of measurement results obtained by a laser surface-inspection device including one incident system and three types of light-receiving systems among which at least one selected from the group consisting of a light-receiving angle and polarization selectivity differs from each other.

In an embodiment, among the above three light-receiving systems, one light-receiving system receives omnidirectional light, while each of the other two light-receiving systems selectively receives polarized light having a different azimuth angle.

In an embodiment, the light-receiving angle of the light-receiving system which receives the omnidirectional light is a higher angle than the light-receiving angles of the other two light-receiving systems.

In an embodiment, when the azimuth angle of the polarized light received by one of the above other two light-receiving systems is designated by $\theta_1°$, and the azimuth angle of the polarized light received by another one is designated by $\theta_2°$, $0° \leq \theta_1° \leq 90°$ and $90° \leq \theta_2° \leq 180°$ are satisfied.

In an embodiment, the first light-receiving system receives omnidirectional light, the second light-receiving system receives polarized light having azimuth angle $\theta_1°$, and the third light-receiving system receives polarized light having azimuth angle $\theta_2°$, wherein the light-receiving angle of the first light-receiving system is a higher angle than the light-receiving angles of the second light-receiving system and third light-receiving system, and on the basis of the determination criteria selected from the group consisting of the presence or absence of detection and detection size in the measurement result 1, the presence or absence of detection and detection size in the measurement result 2, and the presence or absence of detection and detection size in the measurement result 3, it is determined whether the detected abnormality is a process-induced defect or a surface-adhered foreign matter.

In an embodiment, the above determination is performed according to the determination criteria shown in Table 1 described later.

In the above determination criteria, $1.0 < X < 2.0$ is satisfied. In an embodiment, $1.3 < X < 1.6$ is satisfied.

In an embodiment, the incident angle of the above incident light is higher than 0° and less than 90° when all the directions horizontal to the polished surface of a semiconductor wafer are defined as 0° and the direction perpendicular to the polished surface as 90°.

An aspect of the present invention relates to a semiconductor wafer, which has a polished surface and has been evaluated by the above evaluation method.

According to an aspect of the present invention, various types of abnormalities of a semiconductor wafer having a polished surface can be detected.

MODES FOR CARRYING OUT THE INVENTION

Method of Evaluating Semiconductor Wafer

An aspect of the present invention relates to a method (hereinafter, referred to also as "evaluation method") of evaluating a semiconductor wafer having a polished surface by using a laser surface-inspection device including incident and light-receiving systems. The above evaluation method includes evaluating the semiconductor wafer by detecting, as a light point defect, an abnormality selected from the group consisting of a process-induced defect and a surface-adhered foreign matter present on the polished surface of the semiconductor wafer, on the basis of measurement result 1 obtained by directing incident light to the polished surface of the semiconductor wafer from one incident system and receiving, with a first light-receiving system, radiation light which has been radiated by the incident light being reflected or scattered by the polished surface, measurement result 2 obtained by receiving the radiation light with a second light-receiving system, and measurement result 3 obtained by receiving the radiation light with a third light-receiving system, and at least one selected from the group consisting of a light-receiving angle and polarization selectivity differs among the first light-receiving system, the second light-receiving system, and the third light-receiving system.

Hereinafter, the above evaluation method will be described in more detail. In the followings, a semiconductor wafer having a polished surface will be referred to also as a polished wafer.

<Laser Surface-Inspection Device>

A laser surface-inspection device (hereinafter, simply referred to also as "surface inspection device") used in the above evaluation method includes:

one incident system; and three light-receiving systems (first light-receiving system, second light-receiving system, and third light-receiving system) among which at least one selected from the group consisting of a light-receiving angle and polarization selectivity differs from each other.

Figure 1:
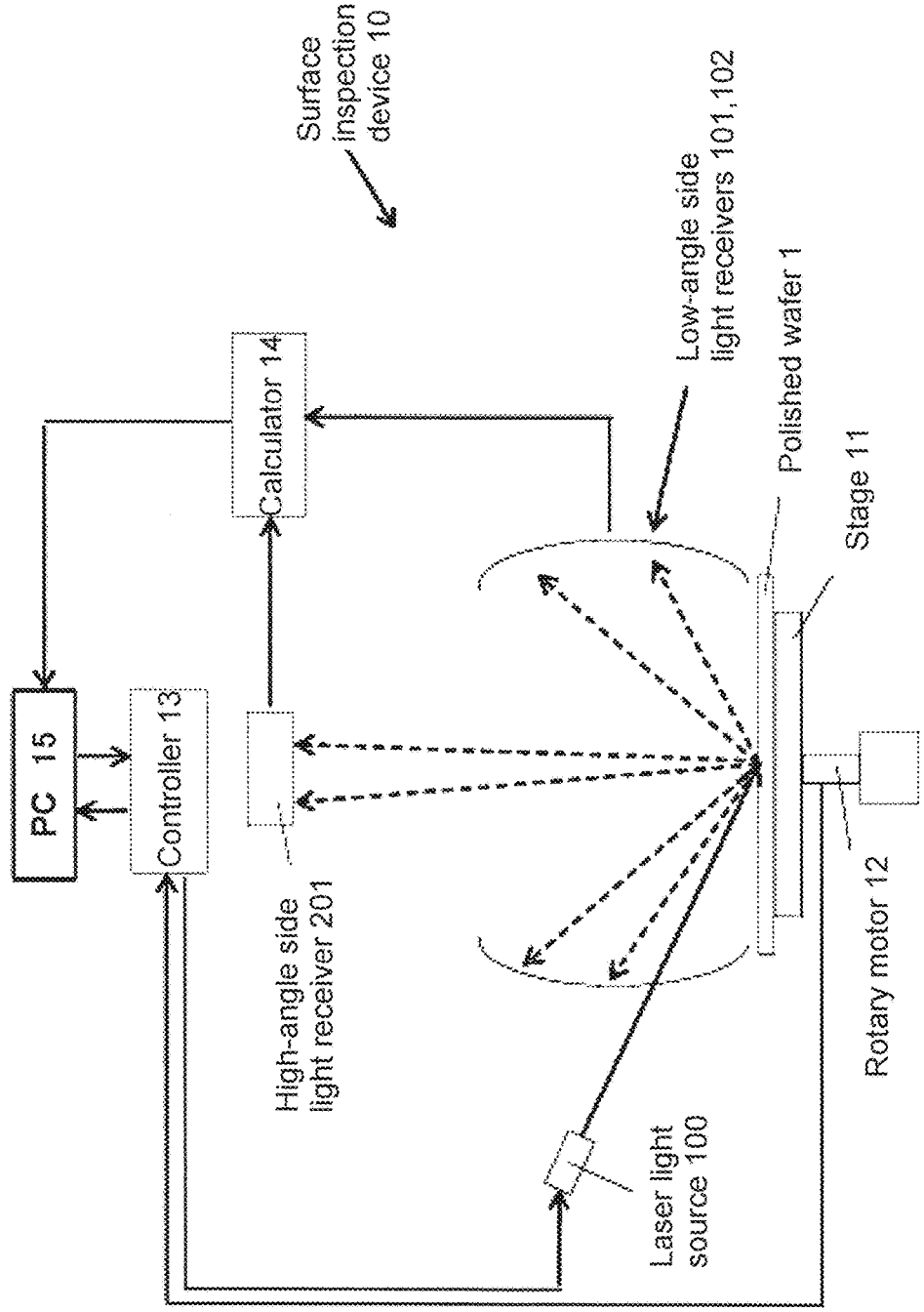
FIG. 1 illustrates an example (schematic configuration diagram) of a laser surface-inspection device.

In such a surface inspection device, the radiation light which has been radiated by the light incident on the polished surface of the semiconductor wafer to be evaluated being reflected or scattered at various places on the polished surface is received by the above three light-receiving systems. The direction in which the radiation light is radiated (specifically, the reflection angle of reflection light or the scattering angle of scattering light) and the polarization characteristic may variously vary with the presence of a process-induced defect and/or surface-adhered foreign matter. The present inventor assumes that by receiving various radiation lights having different radiation directions and polarization characteristics with the three light-receiving systems among which at least one selected from the group consisting of a light-receiving angle and polarization selectivity differs from each other, a process-induced defect and/or surface-adhered foreign matter can be detected as a light point defect. An example (schematic configuration diagram) of a surface inspection device including such an incident system and light-receiving systems is illustrated in FIG. 1. In FIG. 1, although incident light is schematically illustrated with a solid-line arrow and radiation light is schematically illustrated with a dotted-line arrow, the incidence direction and radiation direction illustrated in the figure are exemplary and shall not limit the present invention in any way.

A surface inspection device 10 illustrated in FIG. 1 includes: as an incident system and light-receiving systems,
  a laser light source 100; and
  low-angle side light receivers 101, 102 and a high-angle side light receiver 201 which receive the radiation light radiated by the light incident from the laser light source 100 being scattered or reflected by the surface (polished surface) of a polished wafer 1.

Although the surface inspection device 10 illustrated in FIG. 1 includes one high-angle side light receiver and two low-angle side light receivers, the surface inspection device is not limited to such a configuration and may include two high-angle side light receivers and one low-angle side light receiver. The light-receiving angles of the two low-angle side light receivers may be the same or may differ. This may be true also in the case where there are two high-angle side light receivers. Among these three light receivers, at least one selected from the group consisting of a light-receiving angle and polarization selectivity differs from each other. This point will be further described later. In the surface inspection device 10 illustrated in FIG. 1, the low-angle side light receivers 101 and 102 receive the radiation light in the whole circumference above a stage 11, but the configuration thereof is not limited to the one illustrated in FIG. 1 as far as it is capable of receiving radiation light.

The surface inspection device 10 further includes a rotary motor 12 for making the stage 11 on which the polished wafer 1 is to be placed rotatable, and movable means (not shown) for making the stage 11 movable in the horizontal direction, so that the irradiation position of the light incident from each laser light source can be changed. Thus, it is possible to sequentially irradiate (scan) an area or whole surface to be evaluated on the surface of the polished wafer 1 with light, and detect an abnormality in the area or whole surface to be evaluated.

The surface inspection device 10 further includes a controller 13 configured to control the rotation and movement in the horizontal direction of the stage 11, and a calculator 14 configured to calculate, on the basis of the information about the radiation light detected by each light receiver, the detection size of a detected abnormality. Moreover, a PC (Personal Computer) 15 receives from the controller 13 the position information about the position irradiated with light, and transmits a signal for moving the stage 11 in order to irradiate an un-irradiated position with light. Furthermore, the PC 15 is capable of receiving, from the calculator 14, the information about the detection size of a detected abnormality, and generating the measurement result 1, the measurement result 2, and the measurement result 3.

However, the configuration of the surface inspection device illustrating the outline in FIG. 1 is exemplary. In the above evaluation method, the surface inspection device is not limited to the one with the configuration illustrated in FIG. 1, and various types of surface inspection devices can be used if each is a surface inspection device including one incident system and three light-receiving systems (first light-receiving system, second light-receiving system, and third light-receiving system) among which at least one selected from the group consisting of a light-receiving angle and polarization selectivity differs from each other. For example, as the surface inspection device including one incident system and the above three light-receiving systems, Surfscan series SP5 manufactured by KLA TENCOR Corporation can be used.

<Abnormality to be Detected>

The object to be detected in the above evaluation method is an abnormality selected from the group consisting of a process-induced defect and a surface-adhered foreign matter present on the above polished surface of a semiconductor wafer. These abnormalities are detected as a light point defect in a light-receiving system by directing, from an incident system, light to the polished surface of a polished wafer to be evaluated and by the light being radiated (scattered or reflected) from the polished surface. By detecting the light point defect, the calculator of the surface inspection device can calculate, from the size of the detected light point defect and on the basis of the size of a standard particle, the size (detection size) of an abnormality causing the light point defect. The calculation of the detection size on the basis of the size of a standard particle can be performed by calculation means in a commercially available surface inspection device or with a known calculation method.

A surface-adhered foreign matter is a foreign matter which adhered in the manufacturing process and/or the like of polished wafers, and is usually referred to as Particle.

In contrast, a process-induced defect is introduced into a polished wafer due to a chemical or mechanical processing in the manufacturing process of polished wafers. Examples of the process-induced defect include:

PID (Polished Induced Defect) which is a linear convex defect introduced by polishing, such as in mirror polishing or in the rough polishing (for example, lapping) usually performed before mirror polishing;

Short PID which is a relatively short island-shaped PID among PIDs; and

Shallow which is a relatively smooth concave shaped defect.

<Specific Embodiment of Evaluation Method>

Next, a specific embodiment of the above evaluation method will be described.

(Incident System)

The wavelength of the incident light incident on the polished surface of a polished wafer to be evaluated from one incident system is not particularly limited. The incident light is ultraviolet light in an embodiment, but may be visible light or another light. Here, the ultraviolet light in the present invention means the light in a wavelength region less than 400 nm, while the visible light means the light in a wavelength region from 400 to 600 nm.

The incident angle of the incident light incident on the polished surface of a polished wafer to be evaluated from one incident system may be equal to or greater than 0° and equal to or less than 90° and is preferably higher than 0° and less than 90° when all the directions horizontal to the polished surface are defined as 0°, the direction perpendicular to the polished surface is defined as 90°, and the incident angle is defined as a range from 0° minimum to 90° maximum.

(Light-Receiving System)

As described above, the surface inspection device used in the evaluation method of the present invention includes three light-receiving systems, among which at least one selected from the group consisting of a light-receiving angle and polarization selectivity differs from each other. In an embodiment, one light-receiving system is a high angle light-receiving system which receives, on the high angle side, the radiation light from the polished surface of a polished wafer to be evaluated, while the other two light-receiving systems are low angle light-receiving systems which receive, on the low angle side, the above radiation light. The light-receiving angles of two low angle light-receiving systems may be the same or may be different. Here, the high angle (side)/low angle (side) relative to the light-receiving angle are relatively determined on the basis of a relationship between one angle side and another angle side, and a specific angle shall not be limited. In an embodiment, when the angle is defined, as with the incident angle described earlier, on the basis of the polished surface of a polished wafer to be evaluated, the light reception on the high angle side may refer to the light reception with a light-receiving angle ranging from higher than 80° to equal to or lower than 90°, and the light reception on the low angle side may refer to the light reception with a light-receiving angle ranging from 0° to 80°. Moreover, in another embodiment, two light-receiving systems may be high angle light-receiving systems and one light-receiving system may be a low angle light-receiving system. In this case, the light-receiving angles of two high angle light-receiving systems may be the same or may be different.

At least one selected from the group consisting of a light-receiving angle and polarization selectivity differs from each other among the above three light-receiving systems. The light-receiving angle is as described above. On the other hand, "polarization selectivity differs" means that at least one of a characteristic of selecting and receiving polarized light (i.e., having polarization selectivity), a characteristic of receiving omnidirectional light (i.e., having no polarization selectivity), and a characteristic of selectively receiving polarized light having a specific azimuth angle (or a specific range) among polarized lights differs among light-receiving systems. Means for imparting polarization selectivity to a light-receiving system is well-known. For example, a light-receiving system with polarization selectivity can be constituted by incorporating a polarization filter in the light-receiving system, and a characteristic of selectively receiving polarized light having a specific azimuth angle (or an azimuth angle in a specific range) can be imparted to the light-receiving system according to the type of a polarization filter.

In the above surface inspection device, in an embodiment, one light-receiving system can receive omnidirectional light, while the other two light-receiving systems can selectively receive polarized light. Moreover, in a specific embodiment, one light-receiving system can receive omnidirectional light, while the other two light-receiving systems each can selectively receive polarized light having a different azimuth angle. For two light-receiving systems which selectively receive polarized light, when the azimuth angle of the polarized light received by one light-receiving system is designated by $\theta_1°$ and the azimuth angle of the polarized light received by another one is designated by $\theta_2°$, $0°\leq\theta_1°\leq90°$ and $90°\leq\theta_2°\leq180°$ can be satisfied. Furthermore, in a preferable specific embodiment, the light-receiving angle of the light-receiving system which receives the omnidirectional light can be a higher angle than the light-receiving angle of the light-receiving system which receives polarized light. The omnidirectional light is referred to also as unpolarized light, and is the light which is not polarized light. In contrast, the polarized light is the light having a specific directivity (azimuth angle).

A more preferable specific embodiment of the light-receiving system is as follows:

the first light-receiving system receives omnidirectional light, the second light-receiving system receives the polarized light having azimuth angle $\theta_1°$, the third light-receiving system receives the polarized light having azimuth angle $\theta_2°$, and the light-receiving angle of the first light-receiving system is a higher angle than the light-receiving angles of the second light-receiving system and third light-receiving system.

That is, the first light-receiving system which receives the omnidirectional light is a high angle light-receiving system, while the second light-receiving system and third light-receiving system which receive polarized light are low angle light-receiving systems. Furthermore, the azimuth angles $\theta_1°$ and $\theta_2°$ of the polarized light received by two light-receiving systems (the second light-receiving system and third light-receiving system) which receive polarized light satisfy $\theta_1°\leq\theta_2°$.

The object to be detected in the above evaluation method is an abnormality selected from the group consisting of a process-induced defect and a surface-adhered foreign matter present on a polished surface. Among these abnormalities, the surface-adhered foreign matter (usually referred to as "Particle") tends to isotropically scatter the incident light incident from an incident system as compared with the process-induced defect. In other words, the process-induced defect tends to anisotropically scatter the incident light incident from an incident system as compared with the surface-adhered foreign matter. The present inventor conceives that, regarding such tendency, in a surface inspection device with the light-receiving system according to the more preferable specific embodiment described above, the second light-receiving system which receives polarized light having a lower azimuth angle can suppress the reflected light component from a polished wafer surface (polished surface), and can easily detect the scattering light from the surface-adhered foreign matter which isotropically scatters light. In contrast, the present inventor conceives that the third light-receiving system which receives polarized light having a higher azimuth angle has, as compared with the second light-receiving system, a lower effect of suppressing the reflected light component from a polished wafer surface (polished surface), but can detect, with high sensitivity, the scattering light from a process-induced defect which anisotropically scatters light. Furthermore, the present inventor presumes that, by combining the above second light-receiving system and third light-receiving system with the first light-receiving system which receives the omnidirectional light on the higher angle side than these two light-receiving systems, the detection sensitivity for various types of abnormalities can be further increased. Thus, the present inventor conceives that both the process-induced defect and the surface-adhered foreign matter can be detected with high sensitivity. However, the above discussion includes the presumption of the present inventor and shall not limit the present invention in any way.

As described earlier, since the causes of the process-induced defect and surface-adhered foreign matter differ from each other, the means for reducing these process-induced defect and surface-adhered foreign matter also differs from each other. For example, the surface-adhered foreign matter can be usually removed by washing. Accordingly, the washing may be enhanced in order to reduce the surface-adhered foreign matters. On the other hand, since the process-induced defect is introduced by polishing or the like as described above, a change of the various conditions in the manufacturing process is desirably considered in order to reduce the process-induced defects. Accordingly, in the evaluation of a polished wafer, the surface-adhered foreign matter and the process-induced defect can be desirably discriminated and detected. This is because, by discriminating and detecting, the number of occurrences and/or presence state (distribution) of each of the surface-adhered foreign matter and process-induced defect can be grasped and thus appropriate reducing means can be selected in accordance with the number of occurrences and/or distribution. In this context, with the surface inspection device provided with the light-receiving system according to the above preferable embodiment, whether a detected abnormality is a process-induced defect or a surface-adhered foreign matter can be determined on the basis of the determination criteria selected from the group consisting of:

the presence or absence of detection and detection size in the measurement result 1 obtained by the light reception with the first light-receiving system which receives, on the high angle side, the omnidirectional light;

the presence or absence of detection and detection size in the measurement result 2 obtained by the light reception with the second light-receiving system which receives, on the low angle side, the polarized light having azimuth angle $\theta_1°$; and the presence or absence of detection and detection size in the measurement result 3 obtained by the light reception with the third light-receiving system which receives, on the low angle side, the polarized light having azimuth angle $\theta_2°$ (here $\theta_1°<\theta_2°$).

The present inventor conceives that the reason why such determination is enabled is that the process-induced defect and surface-adhered foreign matter each have a different behavior in scattering and reflecting light due to a difference in the shape and the like caused by a difference in causes and therefore the presence or absence of detection and/or detection size differ among the light-receiving systems each having a different light-receiving angle and/or polarization selectivity.

With the surface inspection device provided with the light-receiving system according to the preferable embodiment described above, whether a detected abnormality is a surface-adhered foreign matter or a process-induced defect can be more preferably determined on the basis of the criteria shown in Table 1 below. In Table 1 below, X satisfies $1.0<X<2.0$. The present inventor conceives that the reason why a process-induced defect and surface-adhered foreign matter can be discriminated by X which satisfies $1.0<X<2.0$ of a relational formula below and the criteria below based on the presence or absence of detection in a specific light-receiving system is due to a difference of the light-receiving angle and/or polarization selectivity of each light-receiving system and also due to a difference in the behavior, between a process-induced defect and a surface-adhered foreign matter, in scattering and reflecting light. This point is a new insight obtained by the intensive study of the present inventor and conventionally not known in any way.

TABLE 1

| Types of abnormalities | Determination criteria |
| --- | --- |
| Surface-adhered foreign matter | detected only in measurement result 2, and not detected in measurement result 1 and measurement result 3, satisfies (detection size in measurement result 3)/(detection size in measurement result 2) < X, or satisfies (detection size in measurement result 1)/(detection size in measurement result 2) < X |
| Process-induced defect | detected in at least one of measurement result 1 and measurement result 3, and not detected in measurement result 2, satisfies (detection size in measurement result 3)/(detection size in measurement result 2) ≥ X, or satisfies (detection size in measurement result 1)/(detection size in measurement result 2) ≥ X |

The X satisfies 1.0<X<2.0, and preferably 1.3<X<1.6. As an example, X=1.4 is established, for example.

A more specific embodiment of the above evaluation method will be described later on the basis of Examples. With the evaluation by the above evaluation method, various types of evaluations on abnormalities, such as the presence or absence of an abnormality on the surface of a polished wafer and the existing number and/or existing position (distribution) of abnormalities, can be performed.

The evaluation can be performed by the above-described evaluation method, and then on the basis of the obtained evaluation results, process changes and/or maintenances (for example, a change in manufacturing conditions, replacement of manufacturing devices, washing, improvement of quality of chemical liquid, and the like.) for reducing various types of abnormalities can be performed on the manufacturing process of polished wafers, so that a high-quality polished wafer with less abnormalities can be subsequently provided as a product wafer.

Moreover, a polished wafer before being shipped as a product can be evaluated by the above evaluation method, and a polished wafer, in which the existing number of various types of abnormalities has been confirmed to fall within a predetermined allowable range (to be equal to or less than a threshold), can be shipped as a product wafer, so that a high-quality polished wafer can be stably supplied. The threshold is not limited in particular, and can be appropriately set in accordance with the application and/or the like of a product wafer.

That is, the above evaluation method can be used for the process control and/or quality control of polished wafers.

[Polished Wafer]

A further aspect of the present invention relates to a semiconductor wafer (polished wafer) which has a polished surface and has been evaluated by the above evaluation method. Such a polished wafer can be a polished wafer, in which the existing number of various types of abnormalities has been confirmed, by evaluation based on the above evaluation results, to fall within a predetermined allowable range (to be equal to or less than a threshold).

EXAMPLES

Hereinafter, the present invention will be further explained on the basis of Examples. However, the present invention is not limited to the embodiments shown in the Examples.

1. Detection of Light Point Defect (LPD) and Calculation of Size of Abnormality

A polished wafer to be evaluated was prepared, and a light point defect was detected using a Surfscan Series SP5 manufactured by KLA TENCOR Corporation as the surface inspection device. The Surfscan Series SP5 manufactured by KLA TENCOR Corporation includes, as one incident system, an ultraviolet light source to cause incident light to be obliquely incident on the surface of a wafer to be evaluated, and includes, as light-receiving systems, three light-receiving systems called a DNO (Dark-Field Narrow Oblique) channel, a DW1O (Dark-Field Wide 1 Oblique) channel, and a DW2O (Dark-Field Wide 2 Oblique) channel. DNO is a light-receiving system which receives omnidirectional light (i.e., without polarization selectivity), and is a light-receiving system on the high angle side relative to the DW1O channel and DW2O channel. On the other hand, the DW1O channel and DW2O channel are light-receiving systems on the low angle side relative to the DNO channel, and have polarization selectivity. The azimuth angle of the polarized light received by the DW1O channel is lower than the azimuth angle of the polarized light received by the DW2O channel. The azimuth angle of the polarized light received by the DW1O channel is equal to or greater than 0° and is equal to or less than 90°, while the azimuth angle of the polarized light received by the DW2O channel is equal to or greater than 90° and is equal to or less than 180°.

Using the surface inspection device Surfscan Series SP5 manufactured by KLA TENCOR Corporation, the whole polished surface of a polished wafer to be evaluated was scanned with incident light to detect an abnormality as a light point defect (LPD), and then on the basis of the size of the light point defect, the detected abnormality size (detection size) was calculated by a calculator in the above surface inspection device. The lower limit (lower limit of detection) of the size of a light point defect detected in each light-receiving system of the above surface inspection device is 36 nm in the DNO channel, 19 nm in the DW1O channel, and 31 nm in the DW2O channel.

2. Observation of Abnormality with Scanning Electron Microscope

Figure 2:
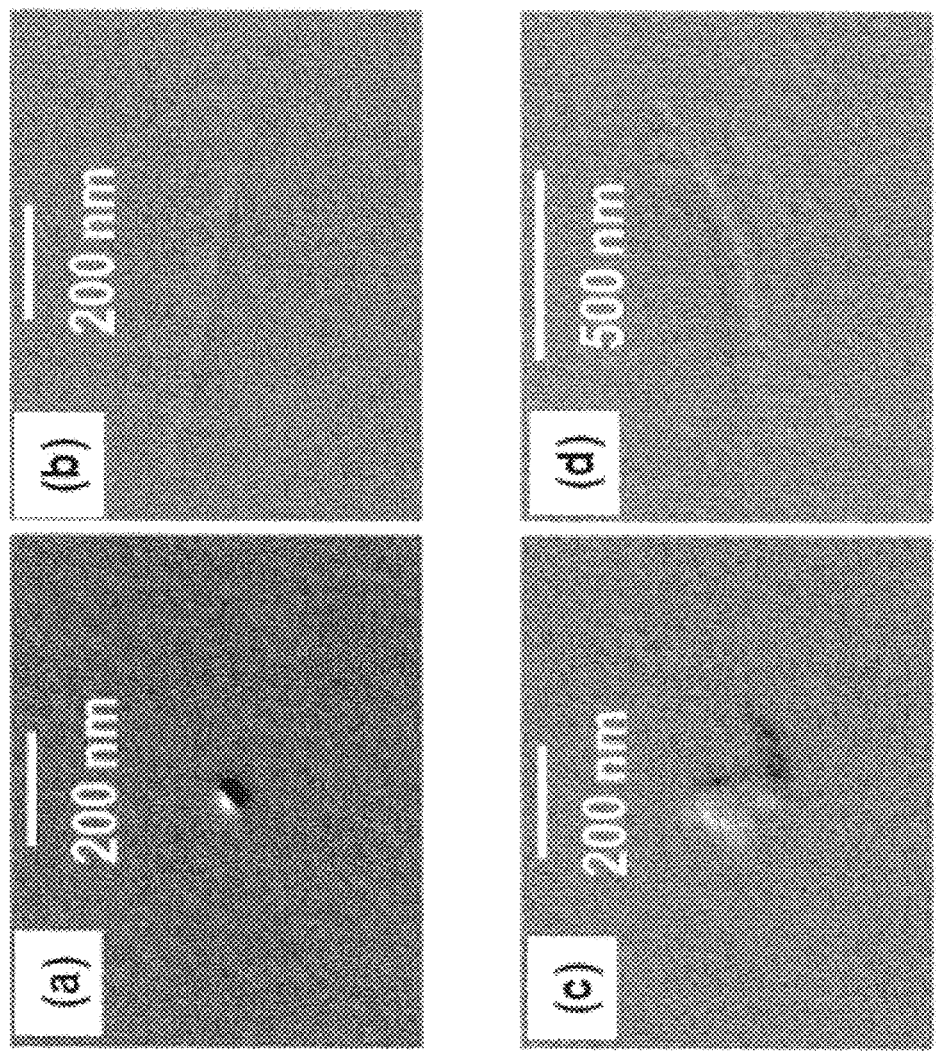
FIG. 2 illustrates various types of abnormalities (SEM images) observed with a scanning electron microscope on the polished surface of a polished wafer evaluated in Examples.

The polished surface of the polished wafer evaluated in the above item 1 was observed with a scanning electron microscope (SEM), and an abnormality present at the position of the light point defect detected by the above surface inspection device was classified into a surface-adhered foreign matter (Particle) and various types of process-induced defects (PID, Short PID, and Shallow) on the basis of the observed shape. An example (SEM image) of each abnormality observed with the SEM is shown in FIG. 2. FIG. 2(a), FIG. 2(b), FIG. 2(c), and FIG. 2(d) are SEM images of abnormalities classified as Particle, as PID, as Short PID, and as Shallow, respectively.

Figure 3:
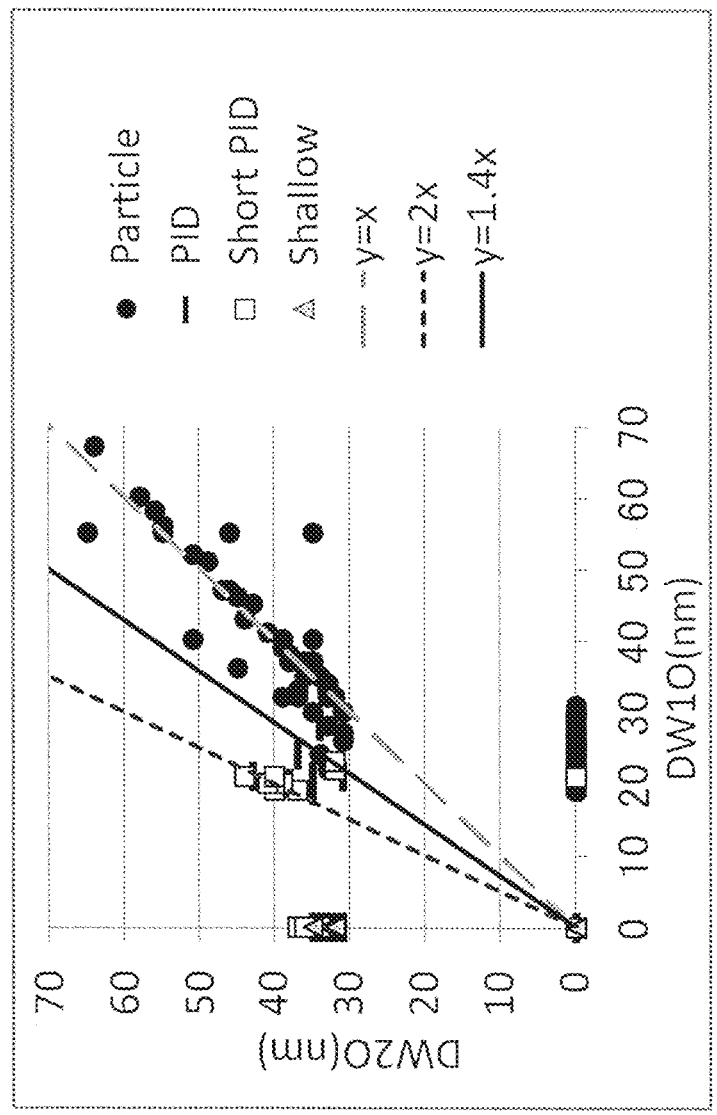
FIG. 3 is a graph illustrating the evaluation results of a polished wafer with a laser surface-inspection device in Examples.

3. Study on Calculated Size and Type of Abnormality (1) Comparison Between the Result Obtained in the DW1O Channel and the Result Obtained in the DW2O Channel FIG. 3 illustrates a graph, in which for each abnormality classified on the basis of the observation by the SEM in the above item 2, the abnormality size calculated from the size detected as a light point defect in the DW1O channel and the abnormality size calculated from the size detected as a light point defect in the DW2O channel in the above item 1 are plotted. In this graph, abnormalities plotted on the X-axis are abnormalities detected only in the DW1O channel and not detected in the DW2O channel, while LPDs plotted on the Y-axis are abnormalities detected only in the DW2O channel and not detected in the DW1O channel.

The following tendencies can be confirmed from the graph illustrated in FIG. 3.

(i) Particle is:
detected only in the DW1O channel (not detected in the DW2O channel), or
the size ratio DW2O/DW1O is approximately 1 (present mainly on the line of y=x or in the periphery thereof);

(ii) PID, Short PID, and Shallow are:
detected only in the DW2O channel (not detected in the DW1O channel), or
the size ratio DW2O/DW1O is approximately 2 (present mainly on the line of y=2x or in the periphery thereof).

(2) Comparison Between the Result Obtained in the DW1O Channel and the Result Obtained in the DNO Channel Then, on the basis of the above results, the abnormality discrimination conditions shown in Table 2 below were prepared. Since the DW2O/DW1O size ratio and DNO/DW1O size ratio of Particle are approximately 1 as well as the DW2O/DW1O size ratio and DNO/DW1O size ratio of the process-induced defects, such as a PID, are approximately 2, it was presumed that the thresholds of the DW2O/DW1O size ratio and DNO/DW1O size ratio were desirably set to greater than 1.0 and less than 2.0, for the discrimination of Particles and the process-induced defect. Thus, they were provisionally set to 1.4. Discrimination was performed using the abnormality determination criteria shown in Table 2, and the validity of the abnormality determination criteria was confirmed by the results of observation by SEM in the above item 2. As the results, there were extremely few abnormalities not compliant with the abnormality determination criteria shown in Table 2, and the compliant ratio calculated by "compliant ratio (%)=[number of compliant abnormalities/(number of compliant abnormalities+number of un-compliant abnormalities)]×100" was higher than 90% as shown in Table 2.

TABLE 2

| Abnormality determination criteria | Determination | Number of abnormalities compliant with determination criteria | Number of abnormalities not compliant with determination criteria | Compliant ratio |
|---|---|---|---|---|
| detected only in DW1O channel (not detected in DW2O channel and in DNO channel), size ratio DW2O/DW1O < 1.4 size ratio DNO/DW1O < 1.4 | Particle | 199 | 2 | 99% |
| detected in DW2O channel and/or DNO channel(not detected in DW1O channel) size ratio DW2O/DW1O ≥ 1.4 size ratio DNO/DW1O ≥ 1.4 | PID Short PID Shallow | 53 | 2 | 96% |

Figure 4:
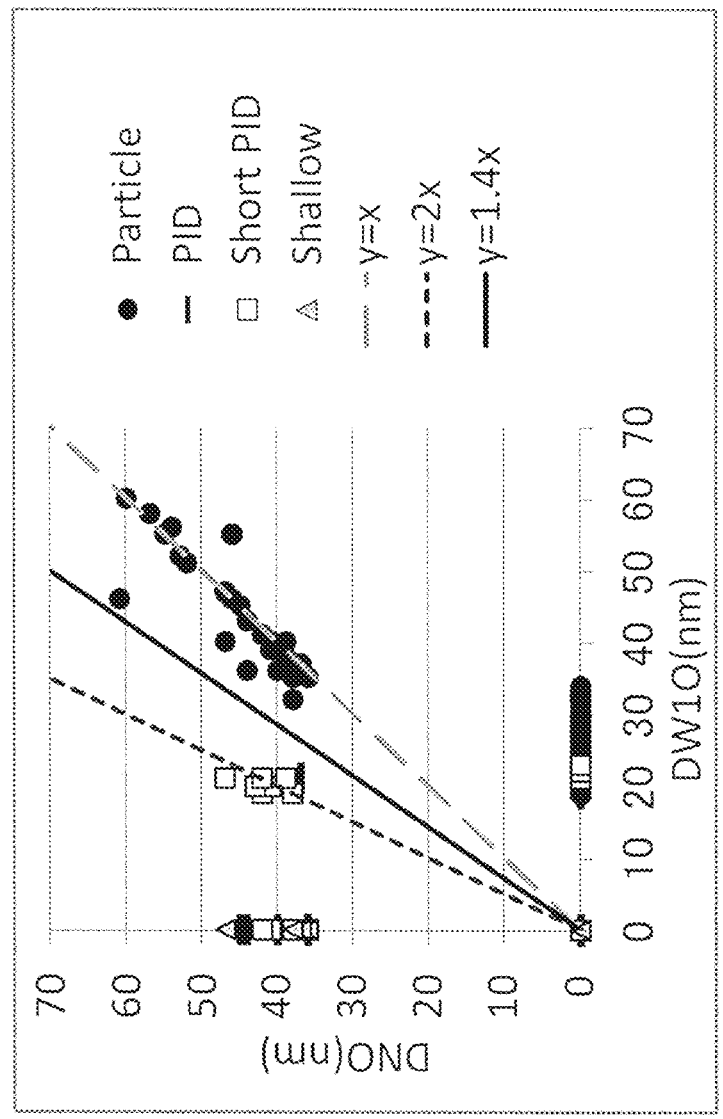
FIG. 4 is a graph illustrating the evaluation results of a polished wafer with a laser surface-inspection device in Examples.

FIG. 4 illustrates a graph, in which for each abnormality classified on the basis of the observation by the SEM in the above item 2, the abnormality size calculated from the size detected as a light point defect in the DW1O channel and the abnormality size calculated from the size detected as a light point defect in the DNO channel in the above item 1 are plotted. In this graph, abnormalities plotted on the X-axis are abnormalities detected only in the DW1O channel and not detected in the DNO channel, while abnormalities plotted on the Y-axis are LPDs detected only in the DNO channel and not detected in the DW1O channel.

The following tendencies can be confirmed from the graph illustrated in FIG. 4.

(i) Particle is:
detected only in the DW1O channel (not detected in the DNO channel), or
the size ratio DNO/DW1O is approximately 1 (present mainly on the line of y=x or in the periphery thereof);

(ii) PID, Short PID, and Shallow are:
detected only in the DNO channel (not detected in the DW1O channel), or
the size ratio DNO/DW1O is approximately 2 (present mainly on the line of y=2x or in the periphery thereof).

As shown in FIG. 3 and FIG. 4, among various types of abnormalities, there is a difference in the size calculated from size of the detected light point defect in the above three light-receiving systems and/or in the presence or absence of detection.

An aspect of the present invention is useful in the field of manufacturing polished wafers.

The invention claimed is:

1. A method of evaluating a semiconductor wafer, which has a polished surface, by using a laser surface-inspection device comprising light-incident and light-receiving systems,
wherein the method comprises evaluating the semiconductor wafer by detecting, as a light point defect, an abnormality selected from the group consisting of a process-induced defect and a surface-adhered foreign matter present on the polished surface of the semiconductor wafer, on the basis of measurement result 1 obtained by directing incident light to the polished surface of the semiconductor wafer from one light-incident system and receiving, with a first light-receiving system, radiation light which has been radiated by the incident light being reflected or scattered by the polished surface, measurement result 2 obtained by receiving the radiation light with a second light-receiving system, and measurement result 3 obtained by receiving the radiation light with a third light-receiving system, and
at least one selected from the group consisting of a light-receiving angle and polarization selectivity differs among the first light-receiving system, the second light-receiving system, and the third light-receiving system, wherein, among the first, second, and third light-receiving systems, one light-receiving system receives omnidirectional light, while each of the other two light-receiving systems selectively receives polarized light having a different azimuth angle, and wherein the light-receiving angle of the light-receiving system which receives the omnidirectional light is larger than light-receiving angles of the other two light-receiving systems.

2. The method of evaluating according to claim 1, wherein the incident angle of the incident light is higher than 0° and less than 90° when all directions parallel to the polished surface of the semiconductor wafer are defined as 0° and a direction perpendicular to the polished surface is defined as 90°.

3. A semiconductor wafer, which has a polished surface and has been evaluated by the method of evaluating according to claim 1.

4. A method of evaluating a semiconductor wafer, which has a polished surface, by using a laser surface-inspection device comprising light-incident and light-receiving systems, wherein the method comprises evaluating the semiconductor wafer by detecting, as a light point defect, an abnormality selected from the group consisting of a process-induced defect and a surface-adhered foreign matter present on the polished surface of the semiconductor wafer, on the basis of measurement result 1 obtained by directing incident light to the polished surface of the semiconductor wafer from one light-incident system and receiving, with a first light-receiving system, radiation light which has been radiated by the incident light being reflected or scattered by the polished surface, measurement result 2 obtained by receiving the radiation light with a second light-receiving system, and measurement result 3 obtained by receiving the radiation light with a third light-receiving system, and at least one selected from the group consisting of a light-receiving angle and polarization selectivity differs among the first light-receiving system, the second light-receiving system, and the third light-receiving system, wherein, among the first, second, and third light-receiving systems, one light-receiving system receives omnidirectional light, while each of the other two light-receiving systems selectively receives polarized light having a different azimuth angle, and wherein, when an azimuth angle of the polarized light received by one of the other two light-receiving systems is designated by $\theta_1°$, and an azimuth angle of the polarized light received by another one of the other two light-receiving systems is designated by $\theta_2°$, $0° \leq \theta_1° \leq 90°$ and $90° \leq \theta_2° \leq 180°$ are satisfied.

5. The method of evaluating according to claim 4, wherein the incident angle of the incident light is higher than 0° and less than 90° when all directions parallel to the polished surface of the semiconductor wafer are defined as 0° and a direction perpendicular to the polished surface is defined as 90°.

6. A semiconductor wafer, which has a polished surface and has been evaluated by the method of evaluating according to claim 4.

\* \* \* \* \*